(12) United States Patent
Dams et al.

(10) Patent No.: US 7,569,715 B2
(45) Date of Patent: *Aug. 4, 2009

(54) COMPOSITIONS CONTAINING SILANES

(75) Inventors: Rudolf J. Dams, Antwerp (BE); George G. I. Moore, Afton, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 343 days.

This patent is subject to a terminal disclaimer.

(21) Appl. No.: 11/466,620

(22) Filed: Aug. 23, 2006

(65) Prior Publication Data

US 2008/0008891 A1 Jan. 10, 2008

Related U.S. Application Data

(63) Continuation-in-part of application No. 11/428,710, filed on Jul. 5, 2006, now abandoned.

(51) Int. Cl.
C07F 7/10 (2006.01)

(52) U.S. Cl. .................... 556/413; 564/80; 564/95; 427/445

(58) Field of Classification Search ............ 556/413
See application file for complete search history.

(56) References Cited

U.S. PATENT DOCUMENTS

| | | | |
|---|---|---|---|
| 2,803,615 A | 8/1957 | Ahlbrecht et al. | |
| 2,809,990 A | 10/1957 | Brown | |
| 3,423,234 A | 1/1969 | Heine | |
| 3,442,664 A | 5/1969 | Heine | |
| 3,492,394 A | 1/1970 | Heine | |
| 3,609,187 A | 9/1971 | Moore et al. | |
| 3,787,351 A | 1/1974 | Olson | |
| 3,906,027 A | 9/1975 | Muessdoerffer et al. | |
| 3,919,295 A | 11/1975 | Wechsberg et al. | |
| 4,167,639 A | 9/1979 | Billenstein et al. | |
| 4,255,299 A | 3/1981 | Daimon et al. | |
| 4,533,713 A | 8/1985 | Howells | |
| 4,557,837 A | 12/1985 | Clark, III et al. | |
| 4,865,910 A | 9/1989 | Inoguchi et al. | |
| 5,207,996 A | 5/1993 | Sierakowski et al. | |
| 5,274,159 A | 12/1993 | Pellerite et al. | |
| 5,342,986 A | 8/1994 | Pohmer et al. | |
| 5,502,251 A | 3/1996 | Pohmer et al. | |
| 5,688,884 A | 11/1997 | Baker et al. | |
| 5,702,509 A | 12/1997 | Pellerite et al. | |
| 5,874,616 A | 2/1999 | Howells et al. | |
| 6,280,883 B1 | 8/2001 | Lamanna et al. | |
| 6,384,168 B1 | 5/2002 | Tanaka et al. | |
| 6,452,038 B1 | 9/2002 | Rao et al. | |
| 6,664,354 B2 | 12/2003 | Savu et al. | |
| 6,689,854 B2 | 2/2004 | Fan et al. | |
| 6,890,452 B2 | 5/2005 | Parent et al. | |
| 6,903,173 B2 | 6/2005 | Cernohous et al. | |
| 6,977,307 B2 | 12/2005 | Dams | |
| 7,078,454 B2 | 7/2006 | Burleigh et al. | |
| 7,160,850 B2 | 1/2007 | Dams et al. | |
| 7,199,197 B2 | 4/2007 | Caldwell et al. | |
| 2003/0224112 A1 | 12/2003 | Dams | |
| 2005/0106326 A1 | 5/2005 | Audenaert et al. | |
| 2005/0142563 A1 | 6/2005 | Haddad et al. | |
| 2006/0147645 A1 | 7/2006 | Dams et al. | |
| 2006/0149012 A1 | 7/2006 | Terrazas et al. | |
| 2007/0149662 A1 | 6/2007 | Qiu | |
| 2008/0113882 A1* | 5/2008 | Arco et al. | ........... 507/205 |

FOREIGN PATENT DOCUMENTS

| | | |
|---|---|---|
| EP | 1 225 187 | 7/2002 |
| GB | 2 218 097 | 11/1989 |
| JP | 60-126203 | 7/1985 |
| WO | WO98/51726 | 11/1998 |
| WO | WO01/30873 | 5/2001 |
| WO | WO02/16306 | 2/2002 |

OTHER PUBLICATIONS

English translation of Yoshioka et al. JP 60-126203.*
"Fluorinated Surfactants—Synthesis, Properties, Applications," Kissa, Marcel Dekker, Inc., Surfactant Science Series, vol. 50.
U.S. Application entitled "Sandstone Having a Modified Wettability and a Method for Modifying the Surface Energy of Sandstone", filed Aug. 23, 2006, having U.S. Appl. No. 11/466,611.

* cited by examiner

*Primary Examiner*—Mark Eashoo
*Assistant Examiner*—Peter F Godenschwager
(74) *Attorney, Agent, or Firm*—Kathleen B. Gross

(57) ABSTRACT

Perfluoro lower alkanesulfonamide-derived silanes which in an organic solvent are useful in treating siliceous substrates are described. The compositions may optionally contain an additional non-fluorinated compound in a mixture or condensation product. Methods for preparing perfluoro lower alkanesulfonamide-derived silanes are also described.

28 Claims, No Drawings

COMPOSITIONS CONTAINING SILANES

CROSS REFERENCE TO RELATED APPLICATION

This application is a continuation-in-part of U.S. application Ser. No. 11/428,710, filed Jul. 5, 2006 now abandoned, the disclosure of which is incorporated herein by reference.

BACKGROUND OF THE INVENTION

Fluorochemical compounds are well known and commercially used to coat or render various substrates oil- and water-repellent and to provide other desirable properties thereto such as soil repellency and soil release.

Fluorochemical alkanesulfonamido silanes having at least 4 carbon atoms in the fluoroalkyl group are known for treating substrates. In addition, fluorochemical oligomeric silanes having at least 4 carbon atoms in the fluoroalkyl group are known for treating hard surfaces, (e.g., glass or crystalline ceramics).

Despite the many known fluorochemical compositions to provide repellency properties to a substrate, there continues to be a desire to find further compositions that may have improved initial repellency properties and/or that have improved durability, (i.e., the repellency properties last longer even under abrading conditions).

SUMMARY OF THE INVENTION

In one aspect, the present invention provides a fluorochemical composition comprising at least one silane of the formula (I):

$$R_{fa}SO_2-N(R)(C_nH_{2n})CHZ(C_mH_{2m})N(R')SO_2R_{fb} \quad\quad I$$

wherein $R_{fa}$ is $C_pF_{2p+1}$, wherein p is an integer from 1 to 5;
$R_{fb}$ is $C_qF_{2q+1}$, wherein q is an integer from 1 to 5, with the proviso that at least one of p or q is 1;
R is a $C_1$ to $C_6$ alkyl group or an aryl group;
m and n are each independently integers from 1 to 20;
Z is selected from the group consisting of hydrogen and a group of the formula —$(C_tH_{2t})$—X-Q-Si$(Y')_w(Y)_{3-w}$, in which t is an integer from 0 to 4; —X— is selected from the group consisting of —O—, —S— and —NH—; -Q- is selected from the group consisting of —C(O)NH—$(CH_2)_v$— and —$(CH_2)_v$—; v is an integer from 1 to 20; Y is a hydrolyzable group; Y' is a non-hydrolyzable group; and w is an integer from 0 to 2; and
R' is selected from the group consisting of a $C_1$ to $C_6$ alkyl group, an aryl group, and a group of the formula —$(CH_2)_v$—Si$(Y')_w(Y)_{3-w}$, with the proviso that when Z is hydrogen, R' is a group of the formula —$(CH_2)_v$—Si$(Y')_w(Y)_{3-w}$.

In another aspect, the present invention includes a fluorochemical composition as above described with an organic solvent in an amount sufficient to dissolve and/or disperse the silane(s).

In another aspect, the present invention provides the above described fluorochemical composition further comprising at least one compound of the formula (II):

$$M(Y')_s(Y)_{r-s} \quad\quad II$$

wherein M is selected from the group consisting of Si, Ti, Zr, Al V, Sn, and Zn;
Y' is a non-hydrolyzable group;
Y is a hydrolyzable group;
s is 0, 1 or 2; and
r is 4, 3 or 2.

In another aspect, the present invention provides the combination of at least one silane of formula I and at least one compound of formula II with an organic solvent in an amount sufficient to dissolve and/or disperse both components.

The present invention also includes methods of treating siliceous substrates by applying to at least a portion of the surface of the substrate a fluorochemical composition comprising at least one silane of formula I and, optionally, at least one compound of formula II in an organic solvent.

In another aspect, the present invention provides methods for making a silane of the formula I. In one embodiment, the present invention provides a method of preparing a silane of the formula $R_{fa}SO_2$—N(R)$CH_2CHZCH_2$N(R)$SO_2R_{fb}$, the method comprising:
reacting (a) a compound of the formula (III):

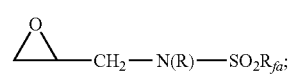

(b) a compound of the formula $R_{fb}$—$SO_2$—NHR, and
(c) a base
to provide a compound of the formula $R_{fa}SO_2$—N(R)$CH_2CH(OH)CH_2$N(R)$SO_2R_{fb}$; and
reacting the compound of the formula $R_{fa}SO_2$—N(R)$CH_2CH(OH)CH_2$N(R)$SO_2R_{fb}$ with a compound of formula W-Q-Si$(Y')_w(Y)_{3-w}$ to provide a compound of the formula $R_{fa}SO_2$N(R)$CH_2CHZCH_2$N(R)$SO_2R_{fb}$;
wherein $R_{fa}$ is $C_pF_{2p+1}$, wherein p is an integer from 1 to 5;
$R_{fb}$ is $C_qF_{2q+1}$, wherein q is an integer from 1 to 5, with the proviso that at least one of p or q is 1;
each R is independently a $C_1$ to $C_6$ alkyl group or an aryl group;
W is selected from the group consisting of I—, Br—, Cl—, and OCN—; and
Z is a group of the formula —O-Q-Si$(Y')_w(Y)_{3-w}$, wherein -Q- is selected from the group consisting of —C(O)NH—$(CH_2)_v$— and —$(CH_2)_v$—; v is an integer from 1 to 20;
Y is a hydrolyzable group; Y' is a non-hydrolyzable group; and w is an integer from 0 to 2.

Compositions according to the present invention are typically efficient and effective oil and water repellents for siliceous surfaces, (e.g., sanitary ceramics, ceramic tiles, and glass). In some embodiments, compositions according to the present invention, which contain two fluorochemical groups, are more effective in creating high oil- and water-repellent surfaces than compositions containing a single fluorochemical group of the same molecular size. In at least some embodiments, compositions according to the invention provide comparable performance to perfluorooctanesulfonamido silanes.

In some embodiments, compositions according to the present invention can be used to modify the wettability of sandstone bearing at least one of oil or gas. In some of these embodiments, the sandstone is a subterranean gas reservoir that is blocked by liquid hydrocarbons (gas condensate) near the well bore. In some instances, the wettability modification increases fluid mobility through the sandstone. When used in oil and/or gas bearing formations, such an increase in fluid mobility may correspond to higher hydrocarbon production for a well located on the formation. For additional details, see copending application U.S. Pat. App. Pub. No. 2007/0197401 (Arco et al.), filed the same date as the instant application.

DETAILED DESCRIPTION

The fluorochemical composition comprises at least one silane of the formula (I):

$$R_{fa}SO_2—N(R)(C_nH_{2n})CHZ(C_mH_{2m})N(R')SO_2R_{fb} \quad \text{I}$$

wherein $R_{fa}$ is $C_pF_{2p+1}$, wherein p is an integer from 1 to 5; $R_{fb}$ is $C_qF_{2q+1}$, wherein q is an integer from 1 to 5, with the proviso that at least one of p or q is 1;

R is a $C_1$ to $C_6$ alkyl group or an aryl group;

m and n are each independently integers from 1 to 20;

Z is selected from the group consisting of hydrogen and a group of the formula —$(C_tH_{2t})$—X-Q-Si$(Y')_w(Y)_{3-w}$, in which t is an integer from 0 to 4; —X— is selected from the group consisting of —O—, —S— and —NH—; -Q- is selected from the group consisting of —C(O)NH—$(CH_2)_v$— and —$(CH_2)_v$—; v is an integer from 1 to 20; Y is a hydrolyzable group; Y' is a non-hydrolyzable group; and w is an integer from 0 to 2; and R' is selected from the group consisting of a $C_1$ to $C_6$ alkyl group, an aryl group, and a group of the formula —$(CH_2)_v$—Si$(Y')_w(Y)_{3-w}$, with the proviso that when Z is hydrogen, R' is a group of the formula —$(CH_2)_v$—Si$(Y')_w(Y)_{3-w}$.

In the fluorochemical composition of the present invention, at least one silane of formula I may be combined (including reacted) with at least one compound of formula (II):

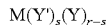
$$M(Y')_s(Y)_{r-s} \quad \text{II}$$

wherein M is selected from the group consisting of Si, Ti, Zr, Al, V, Sn, and Zn;

Y' is a non-hydrolyzable group;

Y is a hydrolyzable group;

s is 0, 1 or 2; and r is 4, 3 or 2.

The perfluoroalkanesulfonamide groups may each contain 1 to 5 carbon atoms and may be linear, branched or cyclic. In some embodiments, the perfluoroalkyl groups, $R_{fa}$ and $R_{fb}$, are both trifluoromethyl, (i.e., p and q are each 1). Alternatively, in some embodiments, $R_{fa}$ is trifluoromethyl, and $R_{fb}$ contains 2 to 5 carbon atoms, (i.e., p is 1 and q is an integer from 2 to 5). In some of these embodiments, $R_{fb}$ contains 4 carbon atoms (i.e., p is 1 and q is 4). Alternatively, in some embodiments, $R_{fb}$ is trifluoromethyl, and $R_{fa}$ contains 2 to 5 carbon atoms, (i.e., q is 1 and p is an integer from 2 to 5). In some of these embodiments, $R_{fa}$ contains 4 carbon atoms (i.e., q is 1 and p is 4).

In some embodiments of the silanes of formula I, m is an integer from 1 to 6 and n is an integer from 1 to 6. In some embodiments of formula I, p and q are both 1, and m and n are each independently integers from 1 to 6. In other embodiments of formula (I), p is 4; q is 1; and m and n are each independently integers from 1 to 6. In some embodiments of formula I, the sum of n and m is 2; X is O; and Q is —C(O)NH$(CH_2)_3$—.

The term "alkyl" as used herein, refers to straight chain, branched, and cyclic alkyl. For example, $C_1$ to $C_6$ alkyl includes methyl, ethyl, propyl, isopropyl, butyl, cyclobutyl, isobutyl, and tertiary butyl. In some embodiments, R and R' are each independently —$CH_3$ or —$CH_2CH_3$. In some embodiments, R and R' are each —$CH_3$. In some embodiments, R is —$CH_3$ or —$CH_2CH_3$.

The term "aryl" as used herein includes aromatic rings or multi-ring systems optionally containing at least one ring heteroatom (e.g., O, S, N). Examples of aryl groups include phenyl, naphthyl, biphenyl, and pyridinyl. Aryl groups may be unsubstituted or may be substituted by up to five substituents (e.g., alkyl, as above defined, alkoxy of 1 to 4 carbon atoms, halo (i.e., fluoro, chloro, bromo, iodo), hydroxyl, amino, and nitro). In some embodiments, when substituents are present, the substituents are halo and alkyl substituents.

In some embodiments of formula I, v is an integer from 1 to 10, and in one embodiment, v is 3.

In some embodiments of formula I, Q is —$(CH_2)_v$—, wherein v is an integer from 1 to 10. In some embodiments, Q is —C(O)NH$(CH_2)_v$— wherein v is an integer from 1 to 10.

In some embodiments of formula I, Z is —O-Q-Si$(Y)_3$, in which each Y is independently —Cl or a $C_1$-$C_4$ alkoxy group. In other embodiments, Z is hydrogen and R' is —$(CH_2)_v$—Si$(Y)_3$, in which each Y is independently —Cl or a $C_1$ to $C_4$ alkoxy group.

The term "hydrolyzable group" in connection with the present invention refers to a group which either is directly capable of undergoing condensation reactions under appropriate conditions or which is capable of hydrolyzing under appropriate conditions, thereby yielding a compound, which is capable of undergoing condensation reactions. Appropriate conditions include acidic or basic aqueous conditions, optionally in the presence of another condensation catalyst, (e.g., Sn-compounds).

The hydrolyzable groups Y may be the same or different and are generally capable of hydrolyzing under appropriate conditions, for example, under acidic or basic aqueous conditions, such that the fluorochemical oligomer can participate in condensation reactions. Preferably, the hydrolyzable groups upon hydrolysis yield groups capable of undergoing condensation reactions, (e.g, silanol groups).

Examples of hydrolyzable groups include halogens (i.e., chlorine, bromine, iodine or fluorine), alkoxy groups —OR" (wherein R" represents a lower alkyl group, preferably containing 1 to 6, more preferably 1 to 4 carbon atoms and which may optionally be substituted by one or more halogen atoms), acyloxy groups —O(CO)—R", aryloxy groups —OR'" (wherein R'" represents an aryl moiety, preferably containing 6 to 12, more preferably containing 6 to 10 carbon atoms, which may be optionally substituted by one or more substituents independently selected from halogens, and $C_1$ to $C_4$ alkyl groups which may optionally be substituted by one or more halogen atoms). In the above formulae R" and R'" may include linear, branched and/or cyclic structures. Specific examples of hydrolyzable groups include methoxy, ethoxy, and propoxy groups and chlorine. In some embodiments, each hydrolyzable group, Y, is independently —Cl or a $C_1$ to $C_4$ alkoxy group. In some embodiments, each Y is independently —Cl, —$OCH_3$ or —$OCH_2CH_3$.

The non-hydrolyzable groups Y' may be the same or different and are generally not capable of hydrolyzing under conditions for condensation reactions, (e.g., acidic or basic aqueous conditions where hydrolyzable groups are hydrolyzed). The non-hydrolyzable groups Y' may be independently a hydrocarbon group, for example, an alkyl group, in some embodiments containing 1 to 4 carbon atoms. In some embodiments, each non-hydrolyzable group, Y', is independently a $C_1$ to $C_6$ alkyl group or an aryl group. In some embodiments, Y' is —$CH_3$ or —$CH_2CH_3$.

In some embodiments of formula II, M is Si; Y' is —$CH_3$ or —$CH_2CH_3$; and each Y is independently —Cl, —$OCH_3$ or —$OCH_2CH_3$.

Representative fluorochemical compounds of the invention include

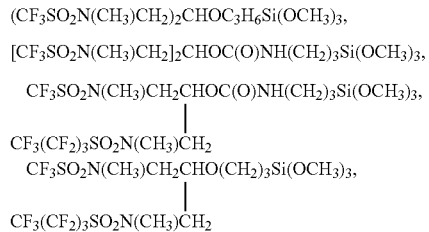

and mixtures thereof. In some embodiments, a fluorochemical composition of the invention comprises at least one of

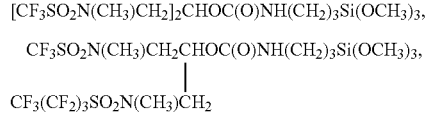

or mixtures thereof. In some embodiments, a fluorochemical composition of the invention comprises at least one of

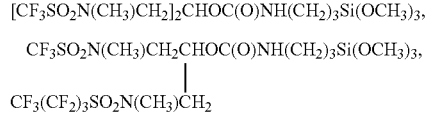

or mixtures thereof.

The fluorochemical compounds of the invention may be prepared by conventional methods. For example, [$CF_3SO_2N(CH_3)CH_2$]$_2$CHOH may be made by reacting two moles of $CF_3SO_2NH(CH_3)$ with either 1,3-dichloro-2-propanol or epichlorohydrin in the presence of base. [$CF_3SO_2N(CH_3)CH_2$]$_2$CHOCH$_2$CH$_2$CH$_2$Si(OCH$_3$)$_3$ can be made from [$CF_3SO_2N(CH_3)CH_2$]$_2$CHOH by alkylation with ClCH$_2$CH$_2$CH$_2$Si(OCH$_3$)$_3$ or by alkylation with allyl chloride, followed by hydrosilation with HSiCl$_3$ and methanolysis. Reaction of [$CF_3SO_2N(CH_3)CH_2$]$_2$CHOH with OCNCH$_2$CH$_2$CH$_2$Si(OCH$_3$)$_3$ yields [$CF_3SO_2N(CH_3)CH_2$]$_2$CHOCONHCH$_2$CH$_2$CH$_2$Si(OCH$_3$)$_3$. Reaction of [$CF_3SO_2N(CH_3)CH_2$]$_2$CHOH with OCNCH$_2$CH$_2$CH$_2$Si(OCH$_2$CH$_3$)$_3$ yields [$CF_3SO_2N(CH_3)CH_2$]$_2$CHOCONHCH$_2$CH$_2$CH$_2$Si(OCH$_2$CH$_3$)$_3$. Reagents used for the preparation of compounds are available from general chemical suppliers such as, for example, Sigma-Aldrich Company, Milwaukee, Wis., or may be synthesized by conventional methods.

A useful intermediate for the preparation of a silane of formula I is a compound of the formula (III):

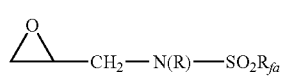
III wherein $R_{fa}$ is $C_pF_{2p+1}$, wherein p is an integer from 1 to 5, and R is a $C_1$ to $C_6$ alkyl group or an aryl group. Intermediates of formula III can be made, for example, by the reaction of a compound of formula $R_{fa}SO_2NH(R)$ with an excess of epichlorohydrin. A particularly useful intermediate of the formula III is N-methyl-N-(oxiran-2-ylmethyl)perfluorobutane-1-sulfonamide. Another particularly useful intermediate of the formula (III) is N-methyl-N-(oxiran-2-ylmethyl)trifluoromethanesulfonamide.

The present invention provides a method of preparing a silane of the formula $R_{fa}SO_2$—N(R)CH$_2$CHZCH$_2$N(R)SO$_2R_{fb}$, the method comprising:
reacting (a) a compound of the formula (III):

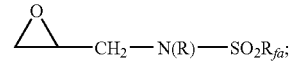
III (b) a compound of the formula $R_{fb}$—SO$_2$—NHR; and
(c) a base
to provide a compound of the formula $R_{fa}SO_2$—N(R)CH$_2$CH(OH)CH$_2$N(R)SO$_2R_{fb}$, and
reacting the compound of the formula $R_{fa}SO_2$—N(R)CH$_2$CH(OH)CH$_2$N(R)SO$_2R_{fb}$ with a compound of formula W-Q-Si(Y')$_w$(Y)$_{3-w}$ to provide a compound of the formula $R_{fa}SO_2N(R)CH_2CHZCH_2N(R)SO_2R_{fb}$.

W is selected from the group consisting of I—, Br—, Cl—, and OCN—; Z is a group of the formula —O-Q-Si(Y')$_w$(Y)$_{3-w}$, wherein -Q- is selected from the group consisting of —C(O)NH—(CH$_2$)$_v$— and —(CH$_2$)$_v$—; v is an integer from 1 to 20; Y is a hydrolyzable group; Y' is a non-hydrolyzable group; and w is an integer from 0 to 2.

In some embodiments of the method, $R_{fa}$ is $C_pF_{2p+1}$, wherein p is an integer from 1 to 5; $R_{fb}$ is $C_qF_{2q+1}$, wherein q is an integer from 1 to 5, with the proviso that at least one of p or q is 1; and R is a $C_1$ to $C_6$ alkyl group or an aryl group. In some embodiments, p is an integer from 2 to 5. In some of these embodiments, p is 4. In some other embodiments, p is 1. In some embodiments, R is a $C_1$ to $C_4$ alkyl group; in some of these embodiments, R is —CH$_3$.

In some embodiments of the method, a compound of formula $R_{fa}SO_2$—N(R)CH$_2$CH(OH)CH$_2$N(R)SO$_2R_{fb}$ is reacted with a compound of formula Hal-(CH$_2$)$_v$—Si(Y')$_w$(Y)$_{3-w}$, wherein Hal is selected from the group consisting of I, Br, and Cl. In other embodiments of the method, a compound of formula $R_{fa}SO_2$—N(R)CH$_2$CH(OH)CH$_2$N(R)SO$_2R_{fb}$ is reacted with a compound of formula OCN—(CH$_2$)$_v$—Si(Y')$_w$(Y)$_{3-w}$.

Reacting the compounds of formulae III and $R_{fb}$—SO$_2$—NHR and a base may be carried out in a suitable solvent (e.g., tetrahydrofuran). The compounds and the base may be combined in any order. The compound of formula III may be added to a solution of a compound of formula $R_{fb}$—SO$_2$—NHR, or a compound of formula $R_{fb}$—SO$_2$—NHR, optionally in a solvent, may be added to a solution of a compound of formula III. Many suitable bases are known to one of skill in the art. The base may be sodium hydroxide, sodium methoxide, or a combination thereof, and may be present as an aqueous solution. The reaction can be carried out by agitating and optionally heating the compounds of formulae III and $R_{fb}$—SO$_2$—NHR and a base. Heating may be carried out at a temperature of at least 50° C., or, in some embodiments, at least 60° C. The temperature may be as high as the reflux temperature of the solvent.

Reacting a compound of formula $R_{fa}SO_2$—N(R)CH$_2$CH(OH)CH$_2$N(R)SO$_2R_{fb}$ with a compound of formula Hal-(CH$_2$)$_v$—Si(Y')$_w$(Y)$_{3-w}$ can be carried out in the presence of base in a suitable solvent (e.g., tetrahydrofuran, methanol, or diglyme). The reaction can be carried out at an elevated temperature (e.g., the reflux temperature of the solvent). The bases described above for the reaction of compounds of formulae III and $R_{fb}$—$SO_2$—NHR can be used. Reacting a compound of formula $R_{fa}SO_2$—$N(R)CH_2CH(OH)CH_2N(R)SO_2R_{fb}$ with a compound of formula OCN—$(CH_2)_v$—Si$(Y')_w$ $(Y)_{3-w}$ may be carried out at room temperature in a suitable solvent (e.g., tetrahydrofuran) in the presence of a catalyst (e.g., dibutyltin dilaurate).

Compositions of the present invention may include at least one organic solvent. The organic solvent or blend of organic solvents used must be capable of dissolving at least one silane of formula I and, optionally, a mixture of at least one silane with at least one compound of formula II.

Suitable organic solvents include aliphatic alcohols, (e.g., methanol, ethanol, isopropanol); ketones (e.g., acetone or methyl ethyl ketone); esters (e.g., ethyl acetate, methylformate); ethers (e.g., diethyl ether or dipropyleneglycol monomethylether (DPM)); and mixtures thereof.

In the combination of silanes of formula I and compounds of formula II, the combination may be a mixture or a condensation product obtainable after a substantially complete condensation reaction of the at least one fluorochemical silane and the at least one non-fluorinated compound of formula II. By the term "substantially complete condensation reaction" is meant that the reaction is either complete or at least 80% of the hydrolyzable groups in the mixture have disappeared, in some embodiments at least 90%. Completion of the reaction can be monitored through the use of infrared spectroscopy, $^{29}$Si-NMR, and $^{13}$C-NMR.

In a further aspect, the present invention provides a composition comprising a condensation product obtainable after a partial condensation reaction of the at least one fluorochemical silane and the at least one non-fluorinated compound. By "partial condensation" and "partial condensate" in connection with the present invention is meant that some of the hydrolyzable groups in the mixture have reacted while leaving a substantial amount of hydrolyzable groups available for a condensation reaction. Typically, a partial condensate means that at least 20%, in some embodiments, at least 30%, and in some embodiments, at least 50% of the hydrolyzable groups are still available for further condensation reaction.

Representative examples of compounds of formula II include tetramethoxysilane, tetraethoxysilane (TEOS), methyltriethoxysilane (MTEOS), dimethyldiethoxysilane (DDS), and tetraethylhexyltitanate.

The combination or condensation product of silanes of formula I and compounds of formula II may also contain organic solvents as defined above in an amount sufficient to dissolve the compounds.

The weight ratio of compounds of formulae I and II is in a range from about 100:0 to about 1:99, in some embodiments, in a range from about 50:50 to about 10:90.

Where the combination of at least one silane of formula I and at least one compound of formula II is a condensation reaction product, the reaction product is obtainable by reacting the components and, optionally, an additional crosslinking agent. Typically, the reaction product is a partial condensate or alternatively a substantial complete condensation product is formed.

The polycondensation reaction is conveniently carried out by mixing the starting components in an organic solvent preferably at room temperature, in the presence of sufficient water to effect hydrolysis of the hydrolyzable groups. In some embodiments, the amount of water can be in a range from 0.1% to 20% by weight of the total composition, or even in a range from 1% to 10% by weight. In addition to water, an organic or inorganic acid or base catalyst should preferably be used.

Organic acid catalysts include acetic acid, citric acid, formic acid, triflic acid, and perfluorobutyric acid. Examples of inorganic acids include sulfuric acid and hydrochloric acid. Examples of useful base catalysts include sodium hydroxide, potassium hydroxide, sodium fluoride, potassium fluoride and triethylamine. The acid or base catalyst will generally be used in amounts in a range from about 0.01% to 10%, in some embodiments in a range from 0.05% to 5% by weight of the total composition.

The composition of the present invention, comprising the components of formulae I and II and optional additional crosslinking agent, and/or the partial or complete polycondensation products thereof, is generally applied to the substrate in amounts sufficient to produce a coating that is water and oil repellent. This coating can be extremely thin, (e.g., 1 to 50 molecular layers, though in practice a useful coating may be thicker).

Suitable substrates that can be treated in a particularly effective way with the fluorochemical composition, comprising the fluorochemical condensate mixture, of this invention include substrates having a hard surface that preferably has groups capable of reacting with the fluorinated condensate. Particularly preferred substrates include ceramics and glass. Various articles can be effectively treated with the fluorochemical composition of the present invention to provide a water and oil repellent coating thereon. Examples include ceramic tiles, bathtubs or toilets, glass shower panels, construction glass, various parts of a vehicle (e.g., mirror or windscreen), and ceramics, (e.g., glass, crystalline ceramic, and enamel pottery materials).

Treatment of the substrates results in rendering the treated surfaces less retentive of soil and more readily cleanable due to the oil and water repellent nature of the treated surfaces. These desirable properties are maintained despite extended exposure or use and repeated cleanings because of the high degree of durability of the treated surface as can be obtained through the compositions of this invention. Additionally, the treated surfaces have a good durability against exposure to UV light, (i.e., the repellency properties do not substantially degrade upon exposure to UV light).

To effect the treatment of a substrate, the fluorochemical composition, preferably in the form of a solvent composition as disclosed above, is applied to the substrate. The amount of fluorochemical composition to be coated on the substrate will generally be that amount sufficient to produce a coating which is water and oil repellent, such a coating having at 20° C. a contact angle with distilled water of at least 80°, and a contact angle with n-hexadecane of at least 40°, measured after drying and curing of the coating. In some embodiments, such a coating has at 20° C. a contact angle with distilled water of at least 85°, and a contact angle with n-hexadecane of at least 45°, measured after drying and curing of the coating.

Preferably, the substrate should be clean prior to applying the compositions of the invention so as to obtain optimum characteristics, particularly durability. That is, the surface of the substrate to be coated should be substantially free of organic contamination prior to coating. Cleaning techniques depend on the type of substrate and include, for example, a solvent washing step with an organic solvent, such as acetone or ethanol.

In accordance with one embodiment, compositions for application to a substrate are prepared by diluting a concentrate comprising a solution of at least 25% by weight of solids in an organic solvent, by adding to the concentrate an organic solvent or mixture of solvents.

A wide variety of coating methods can be used to apply a composition of the present invention, (e.g., brushing, spraying, dipping, rolling, and spreading). In some embodiments, a coating method for application of the fluorochemical composition includes spray application. A substrate to be coated can typically be contacted with the treating composition at room temperature (typically, about 20° C. to about 25° C.). Alternatively, the mixture can be applied to substrates that are preheated at a temperature of, for example, in a range from 60° C. to 150° C. This is of particular interest for industrial production, where, for example, ceramic tiles can be treated immediately after the baking oven at the end of the production line. Following application, the treated substrate can be dried and cured at ambient or elevated temperature, (e.g., at 40° C. to 300° C.) and for a time sufficient to dry and cure. Alternatively, in addition to a thermal treatment, the coating composition may be cured by irradiation (e.g., by means of UV-irradiators, a laser, etc.) in a manner known to one of skill in the art in the presence of an initiator. The process may also require a polishing step to remove excess material.

EXAMPLES

Unless otherwise noted, all parts, percentages, ratios, etc. in the examples and the rest of the specification are by weight.

Coating of Test Solutions

Glass slides were immersed in the test solutions, prepared below, at room temperature for 15 seconds, withdrawn at 0.1 inch per second, and allowed to dry.

Contact Angle Measurement

Advancing and receding contact angles versus water and n-hexadecane were measured on the coated glass slides prepared above using a KRUSS G120/G140 MKI goniometer (Kruss USA, Charlotte, N.C.). Larger values of contact angles indicate better repellency. The values reported below are the mean values of 2 to 4 measurements and are reported in degrees.

Example 1

Preparation of $[CF_3SO_2N(CH_3)CH_2]_2CHOC(O)NH(CH_2)_3Si(OCH_2CH_3)_3$

Part A

A mixture of $CF_3SO_2NHCH_3$ [163 grams (g), 1 mole (mol)] (N-methyltrifluoromethanesulfonamide, generally made as described in U.S. Pat. No. 3,609,187, Example 1), 50% aqueous sodium hydroxide (40.8 g), and tetrahydrofuran (THF) (250 mL) was treated with epichlorohydrin (45.7 g, 0.5 mol) and stirred at 68° C. for about 18 hours. Unreacted $CF_3SO_2NHCH_3$ was present as evidenced by an analysis by gas/liquid chromatography (GLC), and more 50% aqueous sodium hydroxide was added in four 10-g portions, waiting an hour after each. The product mixture was cooled, added to an equal volume of water, extracted with methylene chloride, dried over anhydrous $MgSO_4$, and concentrated to give 167.6 g of an oil, which later solidified. A portion (20 g) was purified by vacuum distillation [boiling point (bp) 192° C./0.5 mmHg (67 Pa)] to provide 16.7 g of $[CF_3SO_2N(CH_3)CH_2]_2CHOH$.

Part B

In a 125-mL bottle, a solution of $[CF_3SO_2N(CH_3)CH_2]_2CHOH$ from Part A (7.6 g, 0.020 mol) in dry THF (40 mL) was treated with $OCN(CH_2)_3Si(OCH_2CH_3)_3$ (5.0 g, 0.020 mol) and dibutyltin dilaurate (2 drops). The reaction was heated at 60° C. in a rotating water bath for 40 hours; analysis by infrared spectroscopy indicated no residual isocyanate was present. The resulting solution containing $[CF_3SO_2N(CH_3)CH_2]_2CHOC(O)NH(CH_2)_3Si(OCH_2CH_3)_3$ weighed 53.4 g and was estimated to contain 23.6% solids.

Test Solution Preparation and Contact Angle Measurement

The solution from Part B (1.0 g) was diluted with ethanol (18 g), concentrated hydrochloric acid (1.0 g of 37%), and isopropanol (5 g) to give a 1% solution. The test solution was coated on a glass slide about one week after it was prepared according to the procedure described above. The advancing and receding contact angles were measured as described above. The advancing and receding contact angles versus water were 84° and 40°, respectively. The advancing and receding contact angles versus n-hexadecane were 44° and 9°, respectively.

Example 2

Preparation of

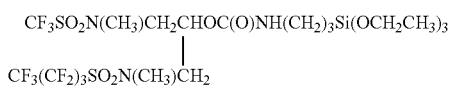

Part A

A mixture of $C_4F_9SO_2NHCH_3$ (313 g, 1.00 mol), generally made as described in U.S. Pat. No. 6,664,354, Example 1, Part A, and sodium methoxide (216 g of a 25% solution in methanol) was concentrated to a solid, which was dissolved in dry THF (500 mL). Epichlorohydrin (120.2 g, 1.3 mol) was rapidly added to the resulting solution, and the mixture was stirred at reflux (64° C.) for 20 hours. The cooled mixture was washed with about 1 L of water, and dichloromethane was used to help transfer the organic fraction. The organic fraction was dried over anhydrous $MgSO_4$, filtered, and concentrated under reduced pressure. The residue was purified by one-plate distillation [bp 90° C./0.06 mmHg (8 Pa)] to provide 155.2 g of N-methyl-N-(oxiran-2-ylmethyl)perfluorobutane-1-sulfonamide, which was 98% pure by GLC.

Part B

A mixture of N-methyl-N-(oxiran-2-ylmethyl)perfluorobutane-1-sulfonamide from Part A (3.7 g, 10 mmol) and N-methyltrifluoromethanesulfonamide (1.70 g, 10.4 mmol) in THF (20 mL) was treated with aqueous sodium hydroxide (0.25 g of 50%), and the reaction was heated in a rotating water bath at 60° C. for 18 hours. The THF was removed under reduced pressure to provide an oil. The oil was triturated twice with hexane to provide 4.8 g of 1-N-methyltrifluoromethanesulfonamido-3-N-methyl perfluorobutanesulfonamidopropan-2-ol as a white solid, mp 79-85° C., which was pure by GLC.

Part C

A hazy solution of 1-N-methyltrifluoromethanesulfonamido-3-N-methyl perfluorobutanesulfonamidopropan-2-ol from Part B (4.2 g, 7.9 mmol) in dry THF (20 mL) was filtered to remove a trace of insoluble material, and the resulting clear solution was treated with $OCN(CH_2)_3Si(OCH_2CH_3)_3$ (1.95 g, 7.9 mmol) and dibutyltin dilaurate (1 drop). The reaction was heated at 40° C. on a steam bath for 30 minutes; analysis by infrared spectroscopy indicated no residual isocyanate was present. The resulting solution containing the title compound weighed 30.2 g.

Test Solution Preparation and Contact Angle Measurement

The solution from Part C (2.0 g) was diluted with ethanol (38 g), concentrated hydrochloric acid (1.0 g of 37%), and isopropanol (1.8 g) to give a 1% solution. The test solution was coated on a glass slide within two days after it was prepared according to the procedure described above. The advancing and receding contact angles were measured as described above. The advancing and receding contact angles versus water were 97° and 40°, respectively. The advancing and receding contact angles versus n-hexadecane were 60° and 37°, respectively.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A fluorochemical composition comprising:
at least one silane of the formula (I):

wherein $R_{fa}$ is $C_pF_{2p+1}$, wherein p is an integer from 1 to 5; $R_{fb}$ is $C_qF_{2q+1}$, wherein q is an integer from 1 to 5, with the proviso that at least one of p or q is 1;

R is a $C_1$ to $C_6$ alkyl group or an aryl group;

m and n are each independently integers from 1 to 20;

Z is selected from the group consisting of hydrogen and a group of the formula $-(C_tH_{2t})-X-Q-Si(Y')_w(Y)_{3-w}$, in which t is an integer from 0 to 4; —X— is selected from the group consisting of —O—, —S— and —NH—; -Q- is selected from the group consisting of —C(O)NH—$(CH_2)_v$— and —$(CH_2)_v$—; v is an integer from 1 to 20; Y is a hydrolyzable group; Y' is a non-hydrolyzable group; and w is an integer from 0 to 2; and R' is selected from the group consisting of a $C_1$ to $C_6$ alkyl group, an aryl group, and a group of the formula —$(CH_2)_v$—Si(Y')$_w$(Y)$_{3-w}$, with the proviso that when Z is hydrogen, R' is a group of the formula —$(CH_2)_v$—Si(Y')$_w$(Y)$_{3-w}$.

2. A composition according to claim 1, wherein p and q are both 1 and m and n are each independently integers from 1 to 6.

3. A composition according to claim 1, wherein p is an integer from 2 to 5; q is 1; and m and n are each independently integers from 1 to 6.

4. A composition according to claim 1, wherein p is 4; q is 1; and m and n are each independently integers from 1 to 6.

5. A composition according to claim 4, wherein Z is —O-Q-Si(Y)$_3$, and wherein each Y is independently —Cl or a $C_1$-$C_4$ alkoxy group.

6. A composition according to claim 5, wherein Q is —$(CH_2)_v$—, wherein v is an integer from 1 to 10.

7. A composition according to claim 5, wherein Q is —C(O)NH($CH_2)_v$— wherein v is an integer from 1 to 10.

8. A composition according to claim 4, wherein Z is hydrogen and R' is —$(CH_2)_v$—Si(Y)$_3$, in which each Y is independently —Cl or a $C_1$ to $C_4$ alkoxy group.

9. A composition according to claim 4, wherein R is —CH$_3$ or —CH$_2$CH$_3$.

10. A composition according to claim 4, wherein the sum of n and m is 2; X is O; and Q is —C(O)NH(CH$_2$)$_3$—.

11. A composition according to claim 1 comprising at least one of

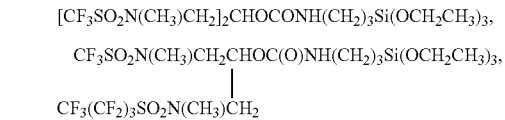

or mixtures thereof.

12. A composition according to claim 1, further comprising an organic solvent.

13. A composition according to claim 12, wherein the solvent is selected from the group consisting of alcohols, ethers, ketones, esters, and mixtures thereof.

14. A composition according to claim 1, further comprising at least one compound of the formula (II):

$$M(Y')_s(Y)_{r-s} \qquad \text{II}$$

wherein M is selected from the group consisting of Si, Ti, Zr, Al, V, Sn, and Zn;
Y' is a non-hydrolyzable group;
Y is a hydrolyzable group;
s is 0, 1 or 2; and
r is 4, 3 or 2.

15. A composition according to claim 14, wherein each Y' is independently a $C_1$ to $C_6$ alkyl group or an aryl group.

16. A composition according to claim 14, wherein each Y is independently —Cl or a $C_1$ to $C_4$ alkoxy group.

17. A composition according to claim 14, wherein M is Si; Y' is —CH$_3$ or —CH$_2$CH$_3$; and each Y is independently —Cl, —OCH$_3$ or —OCH$_2$CH$_3$.

18. A composition according to claim 14, wherein the compound of formula II is tetramethoxysilane, tetraethoxysilane, methyltriethoxysilane, dimethyldiethoxysilane, or tetraethylhexyltitanate.

19. A composition according to claim 14, wherein the compounds of formulae I and II are present in a weight ratio in a range from about 100:0 to about 1:99.

20. A composition according to claim 14, wherein the compounds of formulae I and II are present in a weight ratio in a range from about 50:50 to about 10:90.

21. A fluorochemical composition comprising:
(a) at least one silane of the formula (I):

wherein $R_{fa}$ is $C_pF_{2p+1}$, wherein p is an integer from 1 to 5;
$R_{fb}$ is $C_qF_{2q+1}$, wherein q is an integer from 1 to 5, with the proviso that at least one of p or q is 1;
R is a $C_1$ to $C_6$ alkyl group or an aryl group;
m and n are each independently integers from 1 to 20;
Z is selected from the group consisting of hydrogen and a group of the formula —$(C_tH_{2t})$—X-Q-Si(Y')$_w$ (Y)$_{3-w}$, in which t is an integer from 0 to 4; —X— is selected from the group consisting of —O—, —S— and —NH—; -Q- is selected from the group consisting of —C(O)NH—$(CH_2)_v$— and —$(CH_2)_v$—; v is an integer from 1 to 20; Y is a hydrolyzable group; Y' is a non-hydrolyzable group; and w is an integer from 0 to 2; and
R' is selected from the group consisting of a $C_1$ to $C_6$ alkyl group, an aryl group, and a group of the formula —$(CH_2)_v$—Si(Y')$_w$(Y)$_{3-w}$, with the proviso that when Z is hydrogen, R' is a group of the formula —$(CH_2)_v$—Si(Y')$_w$(Y)$_{3-w}$;

(b) at least one compound of the formula (II):

$$M(Y')_s(Y)_{r-s} \quad \text{II}$$

wherein M is selected from the group consisting of Si, Ti, Zr, Al, V, Sn, and Zn;
Y' is a non-hydrolyzable group;
Y is a hydrolyzable group;
s is 0, 1 or 2; and
r is 4, 3 or 2; and
(c) an organic solvent.

22. A composition according to claim 21, wherein p is 4, and q is 1.

23. A composition according to claim 21 comprising a condensation product of one or more silanes of the formula I and one or more compounds of the formula II.

24. A method of treating a siliceous substrate comprising applying to the substrate a composition according to claim 21.

25. A method of treating a siliceous substrate comprising applying to the substrate a composition according to claim 12.

26. A method of preparing a silane of the formula $R_{fa}SO_2N(R)CH_2CHZCH_2N(R)SO_2R_{fb}$, the method comprising:
reacting (a) a compound of the formula (III):

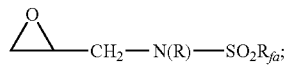

(b) a compound of the formula $R_{fb}$—$SO_2$—NHR, and
(c) a base
to provide a compound of the formula $R_{fa}SO_2$—N(R)$CH_2CH(OH)CH_2N(R)SO_2R_{fb}$; and
reacting the compound of the formula $R_{fa}SO_2$—N(R)$CH_2CH(OH)CH_2N(R)SO_2R_{fb}$ with a compound of formula W-Q-Si(Y')$_w$(Y)$_{3-w}$, to provide a compound of the formula $R_{fa}SO_2N(R)CH_2CHZCH_2N(R)SO_2R_{fb}$;
wherein $R_{fa}$ is $C_pF_{2p+1}$, wherein p is an integer from 1 to 5;
$R_{fb}$ is $C_qF_{2q+1}$, wherein q is an integer from 1 to 5, with the proviso that at least one of p or q is 1;
each R is independently a $C_1$ to $C_6$ alkyl group or an aryl group;
W is selected from the group consisting of I—, Br—, Cl—, and OCN—; and
Z is a group of the formula —O-Q-Si(Y')$_w$(Y)$_{3-w}$, wherein -Q- is selected from the group consisting of —C(O)NH—(CH$_2$)$_v$— and —(CH$_2$)$_v$—; v is an integer from 1 to 20; Y is a hydrolyzable group; Y' is a non-hydrolyzable group; and w is an integer from 0 to 2.

27. The method according to claim 26, wherein p is an integer from 2 to 5, and R is a $C_1$ to $C_4$ alkyl group.

28. The method according to claim 27, wherein p is 4, and R is —CH$_3$.

* * * * *

UNITED STATES PATENT AND TRADEMARK OFFICE
CERTIFICATE OF CORRECTION

PATENT NO. : 7,569,715 B2  Page 1 of 1
APPLICATION NO. : 11/466620
DATED : August 4, 2009
INVENTOR(S) : Rudolf J. Dams It is certified that error appears in the above-identified patent and that said Letters Patent is hereby corrected as shown below:

Column 2

Line 2; delete "Al" and insert -- Al, --, therefor.

Column 12

Line 67; Claim 21, delete " —$(CH_2)_v$—$Si(Y')_w(Y)_{3-w}$.;" and insert -- $(CH_2)_v$—$Si(Y')_w(Y)_{3-w}$; --, therefor.

Signed and Sealed this

Twenty-third Day of November, 2010

David J. Kappos
*Director of the United States Patent and Trademark Office*